(12) United States Patent
Sawada et al.

(10) Patent No.: US 6,255,678 B1
(45) Date of Patent: Jul. 3, 2001

(54) APPARATUS FOR MEASURING PHYSICAL AND CHEMICAL PHENOMENA

(75) Inventors: Kazuaki Sawada, Shizuoka; Katsuhiko Tomita, Miyanohigashi-machi; Tsuyoshi Nakanishi, Miyanohigashi-machi; Hiroki Tanabe, Miyanohigashi-machi; Susumu Mimura, Miyanohigashi-machi, all of (JP)

(73) Assignee: Horiba, Ltd. (JP)

( * ) Notice: Subject to any disclaimer, the term of this patent is extended or adjusted under 35 U.S.C. 154(b) by 0 days.

(21) Appl. No.: 09/085,693

(22) Filed: May 27, 1998

(30) Foreign Application Priority Data

May 29, 1997 (JP) .................................................. 9-157716

(51) Int. Cl.[7] .............................. H01L 29/78; H01J 49/40; G01N 27/00

(52) U.S. Cl. ......................... 257/253; 257/254; 257/414; 257/252

(58) Field of Search .................................... 257/253, 254, 257/414, 252

(56) References Cited

U.S. PATENT DOCUMENTS 5,789,745 * 8/1998 Martin et al. ......................... 250/286

* cited by examiner

*Primary Examiner*—Alexander O. Williams
(74) *Attorney, Agent, or Firm*—Oppenheimer Wolff & Donnelly LLP

(57) ABSTRACT

Method and equipment easily visualize various physical phenomena or chemical phenomena by simultaneously taking in, accumulating, and transferring data at a plurality of points. Electric charge is injected in potential wells constructed to vary the depth in accord with the magnitude of the physical or chemical quantity, and the physical or chemical quantity is converted into electric charge according to the depth of the potential wells.

24 Claims, 12 Drawing Sheets

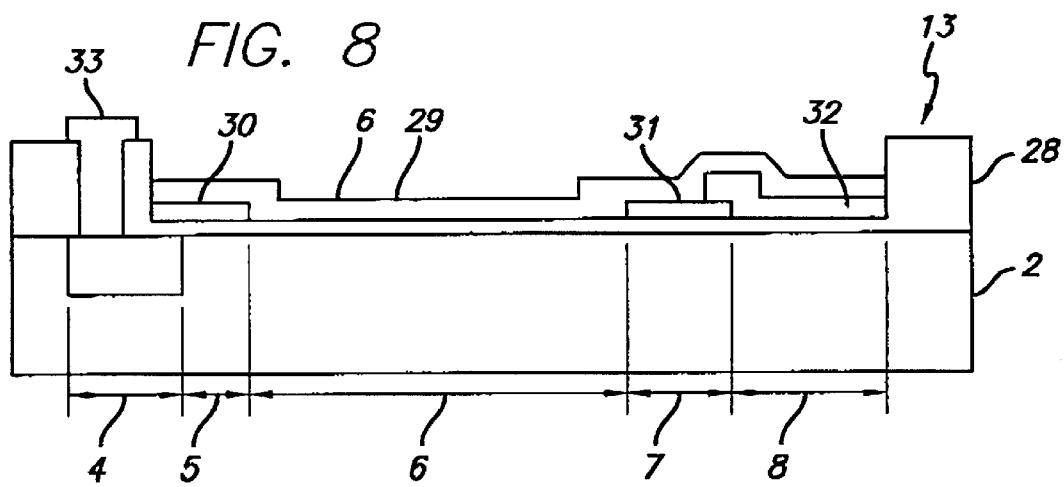
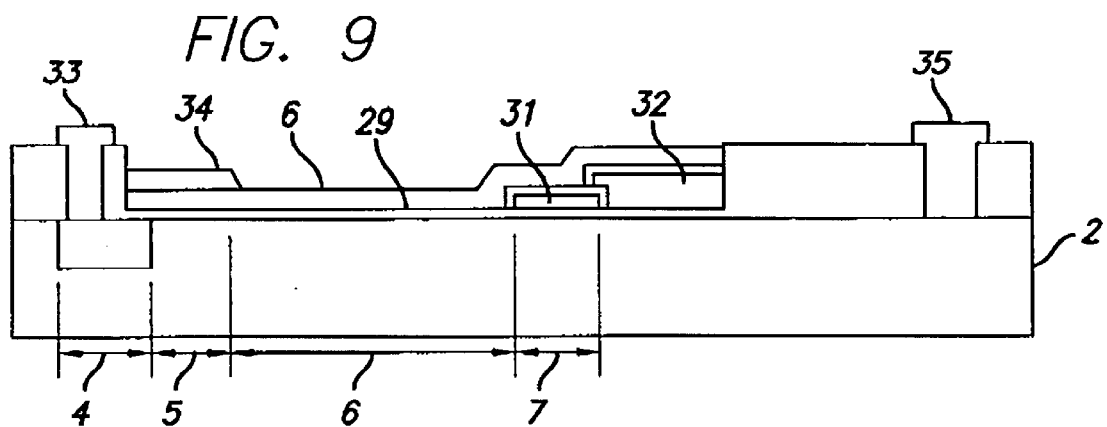
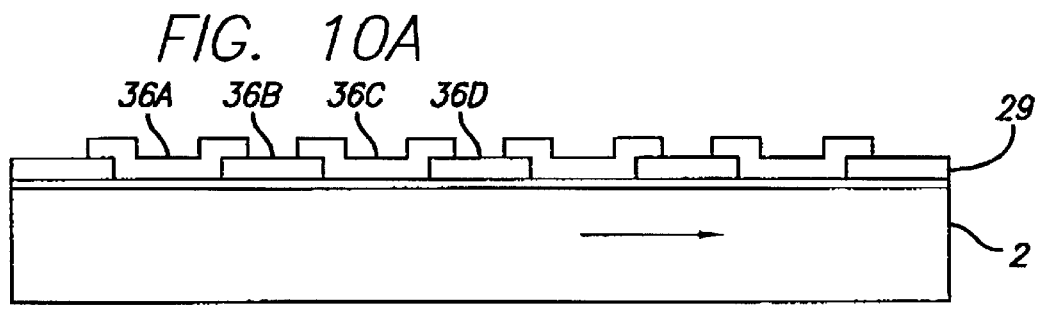
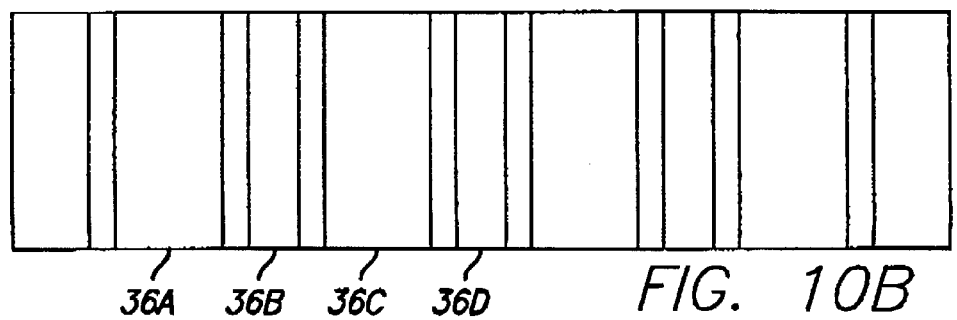

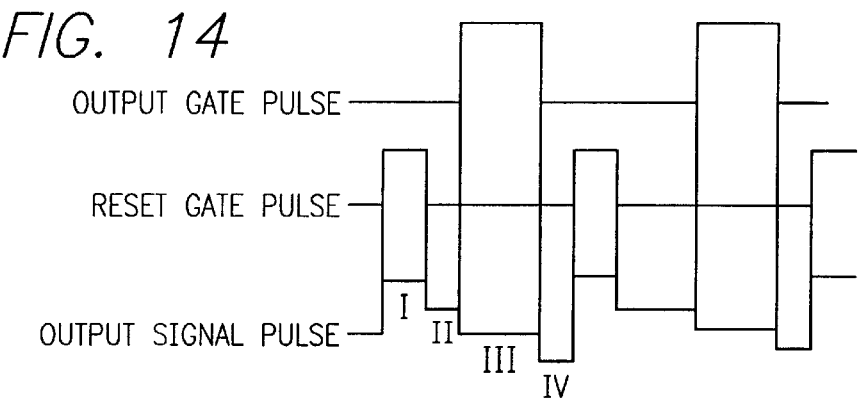
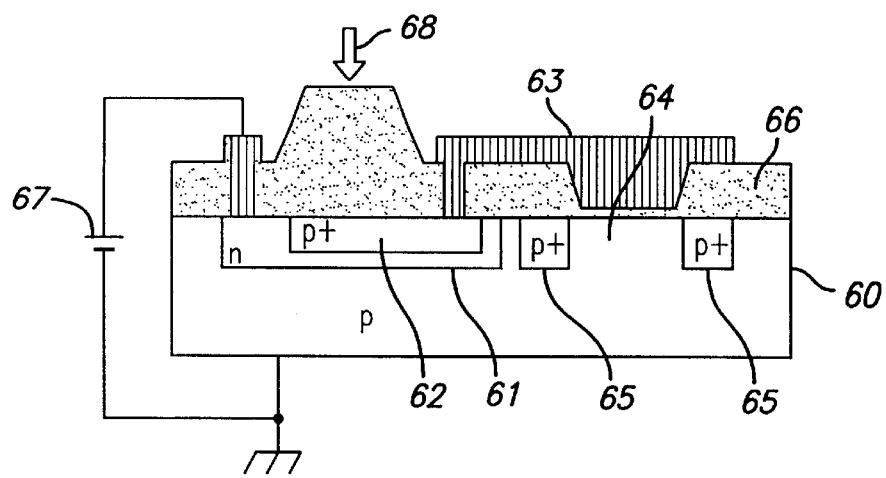
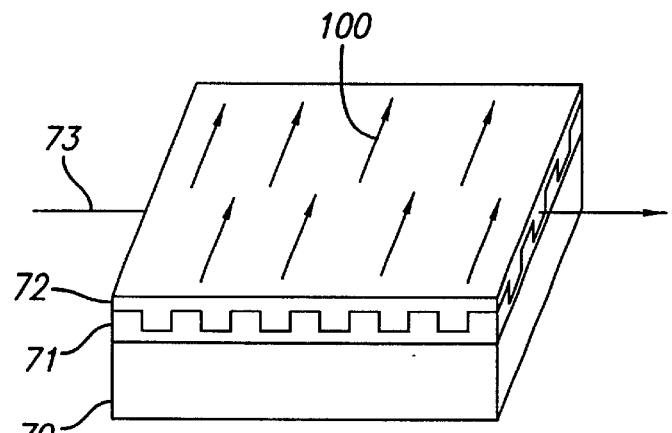

APPARATUS FOR MEASURING PHYSICAL AND CHEMICAL PHENOMENA

BACKGROUND OF THE INVENTION

1. Field of the Invention

The present invention relates to measuring methods and apparatus for quantifying various physical phenomena or chemical phenomena.

2. Description of the Prior Art

Conventionally, light is used to convert physical phenomena or chemical phenomena into electric charges for measurement. Irradiating photo-diodes with the light generates the electron-hole pair corresponding to the light quantity. The light quantity is changed to the quantity of electric charges, and is measured by evaluating the quantity of electric charges. However, in physical and chemical phenomena other than light, in almost all cases, they are converted to electric signals such as voltage values, electric current values, resistance values, etc., and these values are read.

For example, there are thermocouples using the Seebeck effect in which potential difference is generated on both ends when different temperatures are applied to both ends of a certain metal wire. This is intended to join two kinds of different metals, and the temperature of the joined portion is determined from the potential difference generated at both ends. The measurement of pH using an ISFET (ion-sensitive field-effect transistor) is achieved by changing the channel conductance below the pH-sensitive gate insulator by absorbing the hydrogen ion and measuring the pH value of the solution by measuring the drain current in accord with the change.

In either of the measurement methods illustrated above, accumulation and transfer, which are handling methods special to electric charges, are unable to be carried out, and it is extremely difficult to simultaneously take in information at a plurality of points and process at high speed or visualize the measurement results.

SUMMARY OF THE INVENTION

Now, for physical phenomena or chemical phenomena, there are various phenomena such as concentration, temperature, magnetic fields, pressure, acceleration, velocity, sound wave, ultrasonic wave, oxidation-reduction potential, reaction velocity, etc. These phenomena can be converted into various electric signals (current, voltage, resistance, capacity, potential) by the use of conventional technologies. But it is the main object of this invention to handle these phenomena in a manner special to electric charges by converting these phenomena into electric charges and to carry out quantification special to electric charges. More specifically, it is the object of this invention to provide a method and equipment that can easily visualize various physical phenomena or chemical phenomena by simultaneously taking in data at a plurality of points and carrying out accumulation and transfer.

In order to achieve the above objects, the method of measuring physical phenomena or chemical phenomena of this invention is configured to potential wells configured to change the depth corresponding to the magnitude of the physical or chemical quantity, to inject electric charges into these potential wells, and to convert the physical or chemical amount to electric charges corresponding to the depth of the potential wells.

The apparatus of measuring physical or chemical phenomena of this invention is configured to arrayed in a one dimensional or two dimensional manner a plurality of potential wells configured to change the depth corresponding to the magnitude of the physical or chemical quantity, to inject electric charges into these potential wells, and to convert the physical or chemical amount to electric charges corresponding to the data of the potential wells.

By this configuration, it is possible to simultaneously measure phenomena at a plurality of different positions. Because the physical or chemical quantity is converted into electric charges, it is possible to easily visualize the one-dimensional distribution or two-dimensional distribution of physical or chemical phenomena by using a CCD (charge coupled device).

BRIEF DESCRIPTION OF THE DRAWINGS

FIG. 8 is a longitudinal cross-sectional view showing one example of the sensor portion of the above-mentioned equipment;

FIG. 9 is a longitudinal cross-sectional view showing the other example of the sensor portion of the above-mentioned equipment;

FIG. 10A is a longitudinal cross-sectional schematic view illustrating one example of an electric charge transfer section of the above-mentioned equipment, and FIG. 10B is a plan view of the electric charge transfer section shown in FIG. 10A;

FIG. 14 is a graphical view showing signals of each section of the above-mentioned source follower circuit;

FIG. 17 is a longitudinal cross-sectional view schematically showing the equipment according to a second embodiment;

FIG. 18 is a schematic perspective view illustrating the measuring principle of the two-dimensional magnetic field distribution;

DETAILED DESCRIPTION OF THE PREFERRED EMBODIMENTS

Figure 1:
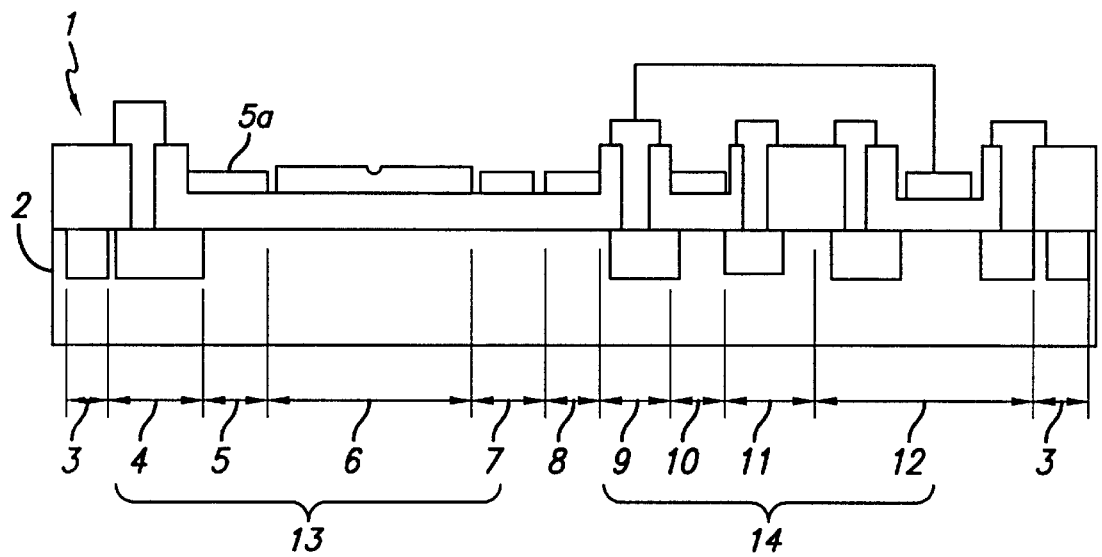
FIG. 1 is a schematic view showing an embodiment of apparatus or equipment for measuring physical phenomena or chemical phenomena in accordance with the present invention.

Referring now to the drawings, preferred embodiments according to the invention will be described in detail hereinafter. First of all, FIG. 1 shows a basic construction of equipment I for measuring physical phenomena or chemical phenomena according to this invention. In this figure, numeral 2 denotes a semiconductor substrate comprising, for example, p-type Si (silicon) which is about 500 $\mu$m thick.

To the semiconductor substrate 2, channel stoppers 3, an electric charge feeder section 4, an electric charge injection controller section 5, a sensing section 6 as electric charge converting section, a barrier section 7, an electric charge transfer section 8, a floating diffusion 9, a reset gate 10, a reset drain 11, and an output transistor of MOS structure 12 are formed.

The sensor section 13 is formed by members of the electric charge feeder section 4, the electric charge injection controller section 5, the sensing section 6, and the barrier section 7. The sensing section 6 comprises potential wells configured to change the depth in accord with the magnitude of the physical or chemical quantity as later discussed. The output section 14 is formed by members of the floating diffusion 9, the reset gate 10, the reset drain 11, and the output transistor 12.

Figure 7:
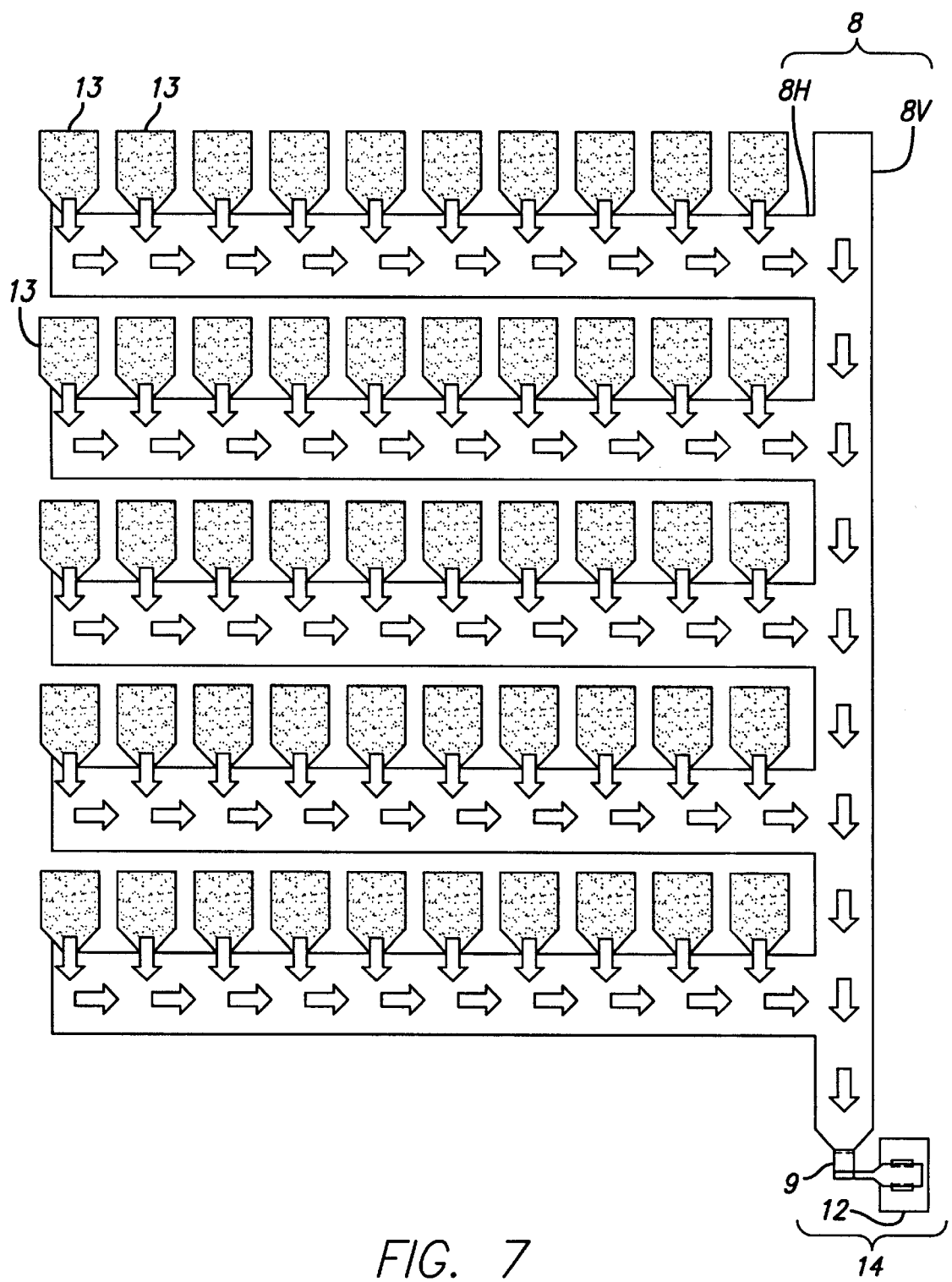
FIG. 7 is a schematic view showing the construction of the principal portion of the above-mentioned equipment.

By arraying the sensor section 13 in a two-dimensional manner as shown in FIG. 7, data at a plurality of points are simultaneously taken in, and the signals at a plurality of points can be orderly processed by the electric charge transfer section 8 and the output section 14. The processing procedure will be later described in detail referring to a number of the embodiments. The sensor section 13 may be one dimensionally arrayed.

Figure 2:
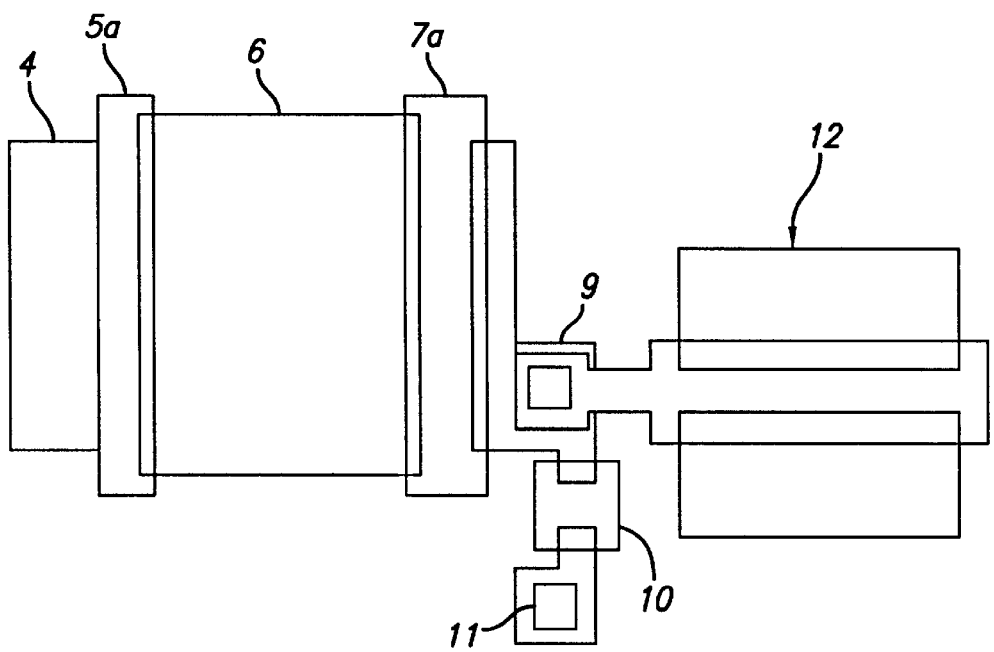
FIG. 2 is a schematic view showing a principal portion of the equipment.

FIG. 2 is an illustration schematically showing the plane configuration of the sensor section 13 and the portion connected to this. In FIG. 2, numeral 5a denotes an electric charge injection controller section electrode, and numeral 7a is a barrier section electrode. The next description will be made on the measuring principle by the measuring equipment referring to the potential diagrams shown in FIGS. 3A–3F. In measurement, the pulse voltage is applied to the electric charge feeder section 4, the barrier section 7, and the reset gate 10, while direct current voltage is applied to other electrodes excluding the floating diffusion 9.

Now, in general, in the MOS structure using the p-type semiconductor, it is known that applying the positive voltage to the metal electrode allows the depletion layer to form at the interface between the insulator and the semiconductor in accord with the voltage. Therefore, using this phenomenon, as shown in FIGS. 3A–3F, the potential condition is formed at the semiconductor-insulation film interface.

Under condition 1, the potential of the electric charge feeder section 4 is set to a high level (higher in the arrow direction), and no electric charge 15 is injected to the sensing section 6.

Under condition 2, as shown in FIGS. 3A–3F, electric charge 15 is charged into the sensing section 6 by lowering the potential of the electric charge feeder section U.

Figure 3A:
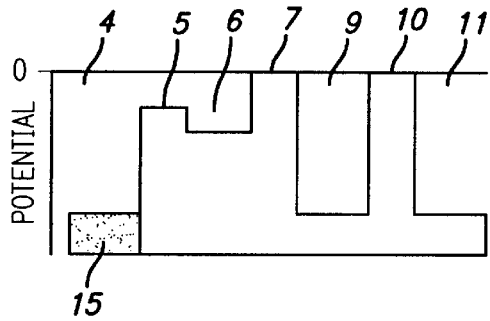
FIGS. 3a–3F are schematic views illustrating measuring methodology of the equipment.
Figure 3D:
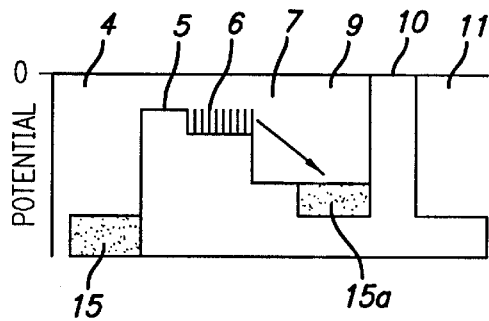
Figure 3B:
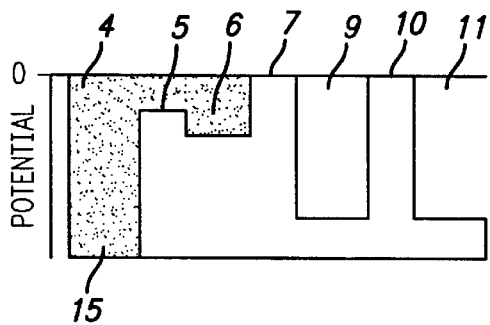
Figure 3E:
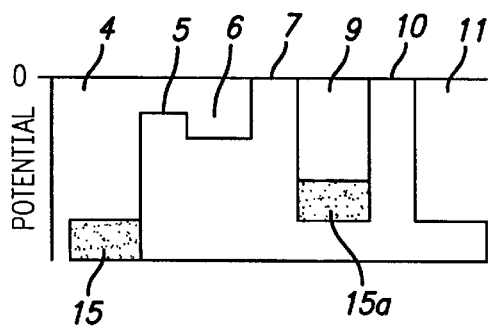
Figure 3C:
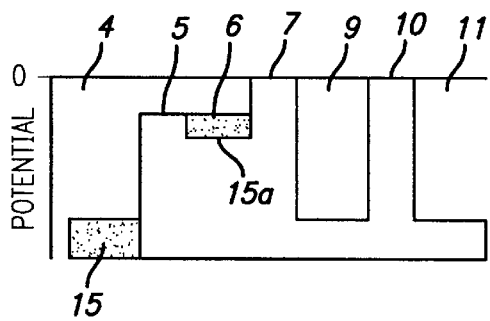

Under condition 3, as shown in FIG. 3C, electric charge 15a leveled off by the electric charge injection controller section 5 is accumulated in the sensing section 6 by raising the potential of the electric charge feeder section 4.

Under condition 4, as shown in FIG. 3D, the electric charge 15a accumulated in the sensing section 6 is transferred to the floating diffusion 9 by raising the potential of the barrier section 7.

Figure 3F:
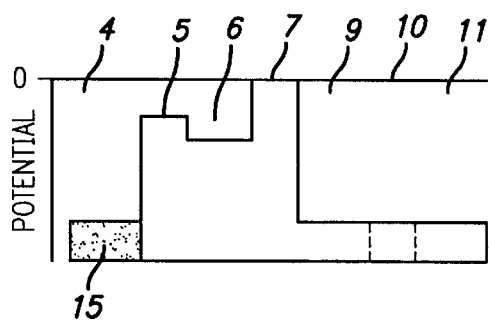
Figure 5:
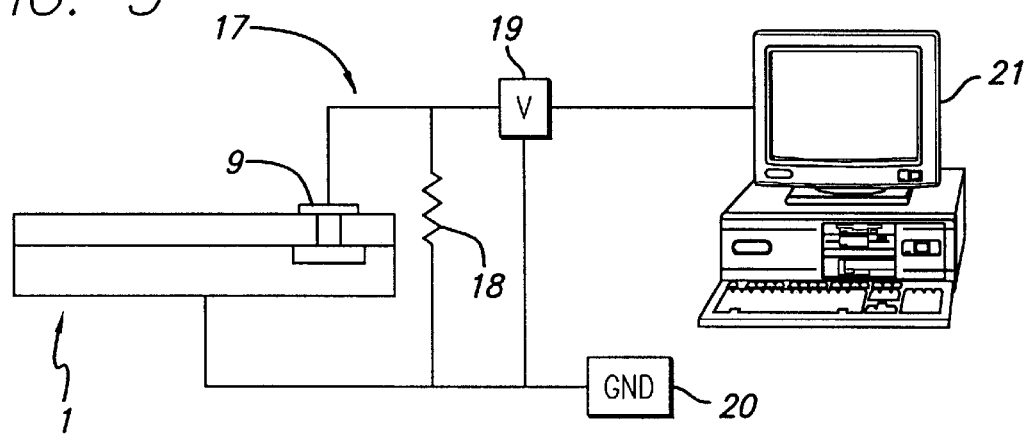
FIG. 5 is a schematic view showing one example of the source follower circuit connected to the above-mentioned equipment.

Under condition 5, as shown in FIG. 3F, the barrier section 7 is closed after all the electric charge 15a of the sensing section 6 is transferred to the floating diffusion 9 and flow-in of electric charge is stopped. Under this stage, the potential of the floating diffusion 9 is determined by the amount of transferred electric charges 15a. This potential is inputted to the gate section of the output transistor 12 of the MOS structure, and the drain current of this output transistor 12 is measured with the source follower circuit 17 as shown in FIG. 5.

Under condition 6, as shown in FIG. 3F, the reset gate 10 is turned on and reset to the potential of the reset drain 11 after the potential of the floating diffusion 9 is read. By this resetting, the condition returns to the same as condition 1 again. That is, repeating the operations of condition 1 to condition 6, electric charge can be outputted to the outside.

Figure 4:
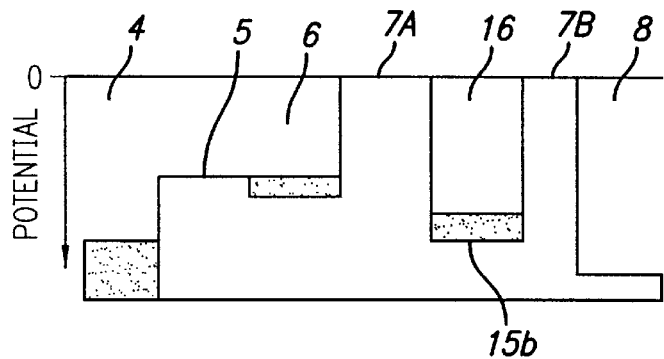
FIG. 4 is a schematic view illustrating additional measuring methodology.

FIG. 4 shows the other embodiment of the measuring equipment. In this measuring equipment, the first barrier section 7A, the electric charge accumulation section 16, and the second barrier section 7B are provided after the sensing portion 6. The electric charge 15b for several terms are accumulated at the electric charge accumulation section 16, and after a certain amount of electric charge is accumulated, the potential of the second barrier section 7B is raised. The electric charges accumulated at the electric charge accumulation section 16 are transferred to the electric charge transfer section 8. In the measuring equipment configured in this way, the sensitivity increases several times, and it is possible to carry out measurement at higher accuracy.

As understood from the explanation concerning FIGS. 3A–3F and FIG. 4. in this measuring equipment, there is used an electric charge conversion mechanism for (1) forming potential wells (sensing section 6) configured to vary the depth in accordance with the magnitude of the physical or chemical quantity on the semiconductor substrate 2, (2) injecting electric charges 15 to the potential wells 6, and (3) converting the physical or chemical quantity to electric charges in accordance with the depth of these potential wells.

In the measuring equipment shown in FIGS. 3A–3F and FIG. 4, the potential of the electric charge feeder section 4 is raised and lowered to level off the electric charges accumulated at the sensing section 6. But in place of this configuration, it is allowed to hold the potential of the electric charge feeder section 4 constant, raise and lower the level of the electric charge injection controller section 5, and level off electric charge accumulated at the sensing section 6.

Figure 13:
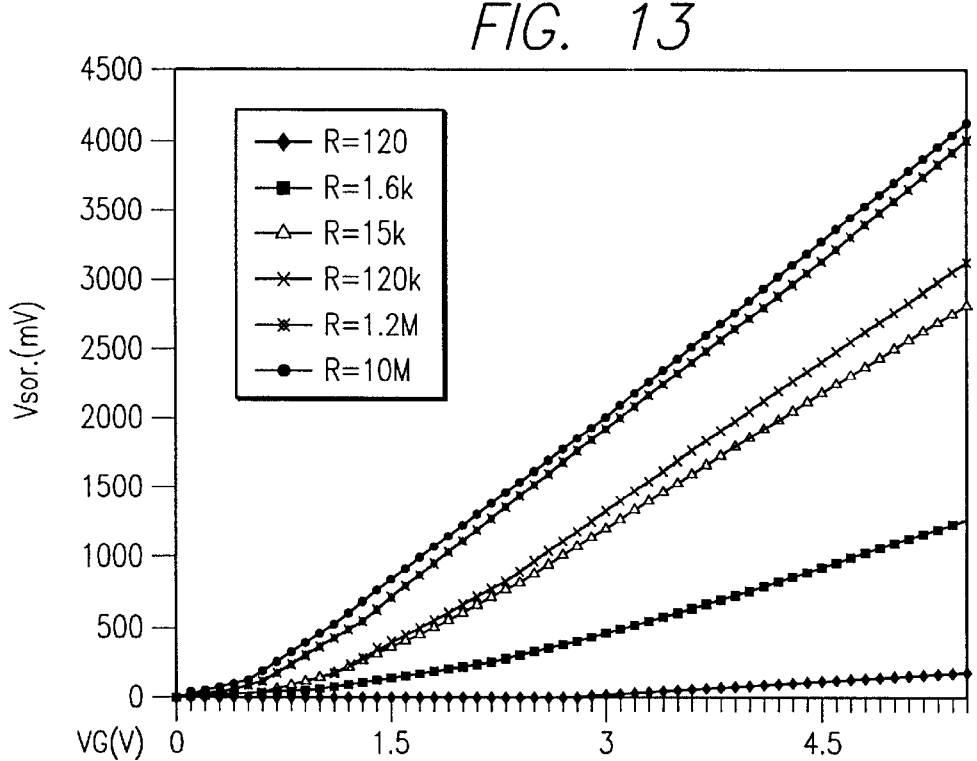
FIG. 13 is a graphical view showing the characteristics of the source follower circuit.

FIG. 5 shows one example of the source follower circuit 17, which comprises a resistor 18, an output terminal 19, and a grounding terminal 20. The output signal in this circuit 17 greatly varies in accord with the size of the resistor 18 connected as shown in FIG. 13, but linear voltage signals can be obtained with respect to the output current. Numeral 21 designates a monitor equipped with data processing capabilities or image processing capabilities connected to the output terminal 19.

Figure 6:
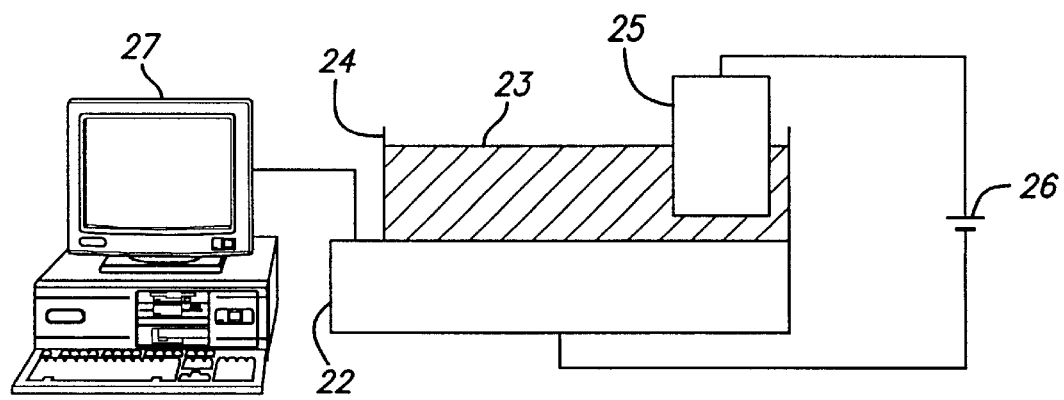
FIG. 6 is a schematic view including a longitudinal cross-sectional view showing the equipment according to a first embodiment.

Referring now to FIG. 6 and after, various measuring equipment with the electric load conversion mechanism built in will be explained.

For a first embodiment, description will be made on equipment for measuring the two-dimensional distribution of the pH of the solution. FIG. 6 schematically shows a two-dimensional distribution measuring equipment of pH of the solution. In FIG. 6, numeral 22 is a substrate, the top surface of which a cell 24 for accommodating a sample 23 such as the solution is formed. This substrate 22 imparts water resisting property to the sample 23 by providing resin mold. Numeral 25 is a reference electrode immersed in the sample 23, and by applying a specified voltage across the substrate 22 by the direct current power supply 26, this reference electrode 25 brings the potential of the sample 23 to a specified high level with respect to the substrate 22. The applied voltage causes the sensing section 6 to be in the depleted condition.

In the pH two-dimensional distribution measuring equipment of the above-mentioned configuration, the outputted signals are inputted as they are to the image output unit 27 such as monitors, displays, etc. to output images, or the output signals may be AD-converted to be inputted to a computer.

FIG. 7 schematically shows the configuration of the top surface of the substrate 22, which comprises a plurality of sensor sections 13 for converting the pH to electric charges, an electric charge transfer section 8 for transferring electric charges converted at the sensor section 13 in the arrow direction, and an output section 14 for converting the transferred electric charges into output signals. The electric charge section 8 comprises horizontal CCD 8H and vertical CCD 8V.

FIG. 8 shows the construction of the sensor section 13. This sensor section 13 is formed as follows. That is, the p-type Si substrate 2 which is made to be the substrate 22 is thermal oxidized to form the oxide film ($SiO_2$) 28, and part of the oxide film is etched and further thermal oxidized to form the gate oxide film 29. The film thickness of this gate oxide film 29 is about 500 Å, and electrodes 30, 31 are formed by depositing low-resistance P-doped poly-silicon to the portions corresponding to the electric charge injection controller section 5 and the barrier section 7 on the top surface, respectively. The film thickness of these electrodes 30, 31 is about 3000 Å, and the film is thermal oxidized to about 1000 Å after deposition. Thereafter, the P-doped low-resistance poly-silicon is deposited again and the electrode 32 is formed on the top surface of the electric charge transferring section 8. The film of this electrode 32 is thermal oxidized to about 1000 Å after poly-silicon is deposited to the level similar to that of the electrodes 30, 3 1. Oxidizing the film in this way can hold insulation between electrodes. Thereafter, $Si_3N_4$ ($Ta_2O_3$ or $Al_2O_3$ acceptable) is accumulated to about 700 Å to form the sensing section 6. Numeral 33 designates an electrode formed with aluminum.

FIG. 9 shows the other embodiment of the sensor section 13, and in the sensor section 13 shown in FIG. 9, a reference electrode is incorporated. That is, in this sensor section 13, in place of the electrode 30 of the electric charge injection controller section 5 shown in FIG. 8, a film 34 which is not sensitive to pH is installed. And the threshold value of the sensing section 6 is adjusted and the potential wells of the sensing section 6 are made deeper as compared to the electric charge injection controller section 5. In order to achieve electric connections between the sample and the substrate, an electrode 35 comprising inert metal such as platinum, etc. is installed. The electric charge injection controller section 5 and the sensing section 6 are designed to allow the sensing section 6 only to respond to the pH and not to allow the electric charge injection controller section 5 to respond, but both are equally subject to influences such as external noise or potential variations at an interface between the electrode 35 and the sample. That is, the difference of potential between the electric charge injection controller section 5 and the sensing section 6 reflects the pH value. Consequently, injecting electric charges to the sensing section 6 can convert the pH value to electric charges.

Now description will be made on the width of the electrodes 30 to 33, 35 and he sensing section 6. First of all, because the electric charge injection controller section 5 is the portion that serves to allow the electric charge fed from the electric charge feeder section 4 to be leveled off by the sensing section 6, about 10 $\mu$m is sufficient for the width of the electrodes 30 to 33, 35. The barrier section 7 only works to prevent electric charges leveled off by the sensing section 6 from flowing into the electric charge transferring section 8 readily, and about 10 $\mu$m is sufficient for the width.

For the sensing section 6, because a certain amount of electric charge to be leveled off is required in order to improve the measuring accuracy, the minimum required area is secured for the purpose, and it has a size of about 10$\mu$ by about 10 $\mu$m to about 100 $\mu$m by 100 $\mu$m. For the size of this sensing section 6, various sizes are set with the electric charge transferring section 8 and the floating diffusion 9 taken into account. Experimentally, the sizes of the sensing section 6, the electric charge transferring section 8, and the floating diffusion 9 were designed to be about 100 $\mu$m by 100 $\mu$m, 50 $\mu$m by 200 $\mu$m, 21000 $\mu m^2$, respectively, and measurement was carried out. In the source follower circuit 17 using a 120 k$\Omega$ resistor 18 (see FIG. 5), about 80 mV output signals have been obtained per 1 pH.

FIGS. 10A and 10B show one example of the configuration of the electric charge transferring section 8, and wherein FIG. 10A shows a cross-sectional structure and FIG. 10B shows a top surface structure. The electric charge transferring section 8 shown in FIG. 10 comprises a CCD of a 4-phase structure, and by depositing P-doped low-resistance poly-silicon in two layers in about 3000 Å thickness on the top surface of the oxide film 29, four electrodes 36A, 36B, 36C, 36D are formed. Each of the electrodes 36A to 36D are oxidized to about 1000 Å in order to achieve insulation one another.

Figure 11:
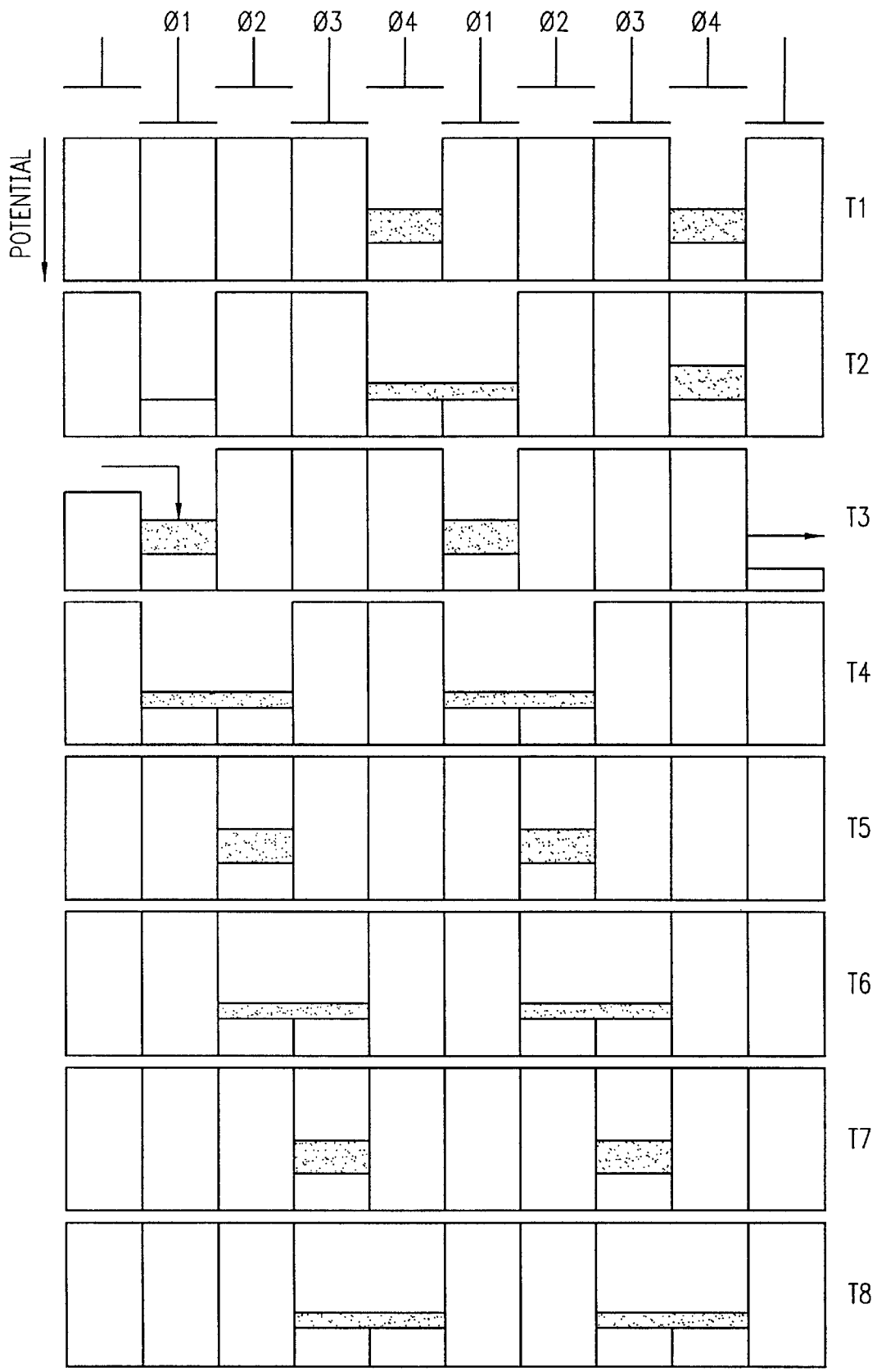
FIG. 11 is a graphical view of a CCD drive potential diagram of the above-mentioned electric charge transfer section.
Figure 12:
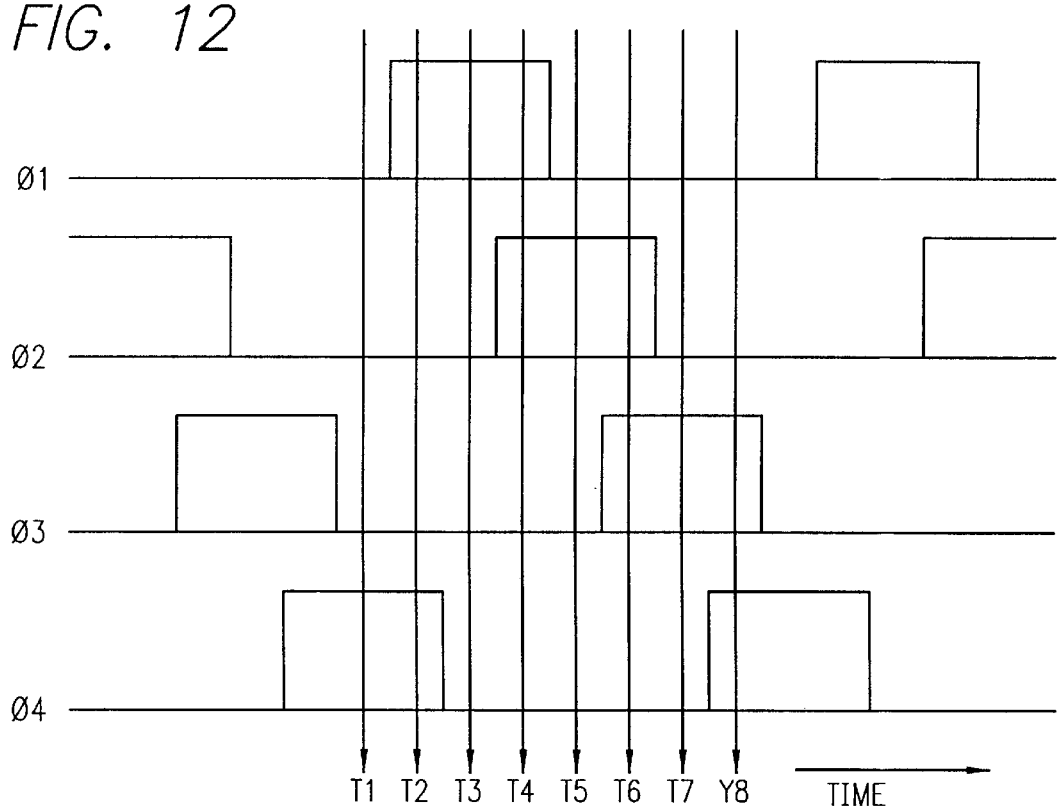
FIG. 12 is a graphical view of a timing chart of CCD drive voltage of the above-mentioned electric charge transfer section.

FIG. 11 and FIG. 12 are illustrations for explaining the drive principle of the electric charge transferring section 8. In particular, FIG. 11 shows the CCD driving voltage of the electric charge transferring section 8, and FIG. 12 is a timing chart of the CCD driving voltage. Symbols $\phi$ 1to $\phi$ 4 in FIGS. 11, 12 and 13 correspond to 36A to 36D, respectively.

The CCD drive in the electric charge transferring section 8 is not limited to the four phases, but a one-phase drive, a two-phase drive, etc. may be accepted and suitably selected in accord with the electric charge amount to be transferred. As the number of the sensor section 13 increases, the transfer efficiency may cause problems, but in such event, it is preferable to use a bulk channel with high transfer efficiency.

The electric charge transferred by the electric charge transferring section 8 is transferred to the floating diffusion 9 (see FIG. 7) of the output section 14, and varies the potential of the floating diffusion 9. This potential variation is inputted to the gate of the output transistor 12, and the drain current of the output transistor 12 is read by the source follower circuit 17 (see FIG. 5).

FIG. 13 shows characteristics of the source follower circuit 17, and this data is obtained when the MOS transistor of 200 μm in channel width and 50 μm in channel length is used for an output transistor 12 and the resistor 18 is set to various values. FIG. 13 indicates that by changing the value of the resistor 18 in the source follower circuit 17, the output value of the source follower circuit 17 is considerably changed.

Now, in measuring the pH, to improve the measuring accuracy, a large change of output should be obtained with respect to the change in the amount of electric charges transferred to the floating diffusion 9. To achieve this, the area of the floating diffusion 9 should be made as small as possible, but an excessively small area is easily saturated when incoming electric charge is excessive and measurement is unable to be carried out. Consequently, it is preferable to determine the area of the floating diffusion 9 and the resistance 18 in the source follower circuit 17 by the area of the sensing section 6 as well as drive voltage of the electric charge transferring section 8.

FIG. 14 shows the output signal pulse of the source follower circuit 17 together with the output gate pulse and the reset gate pulse. The output signal pulse is outputted in a complicated form as shown in FIG. 14, but the true signal is the portion shown with symbol IV in the figure. That is, the portion of symbol I is the pulse signal generated when the reset gate is turned on, and is the signal generated as long as the reset gate 10 is superimposed on the floating diffusion 9. The portion of symbol II is the signal under the electrically floating condition after the floating diffusion 9 is reset. The signal of symbol III is the pulse signal generated when the output gate is turned on.

The signal expressed by symbol IV is the signal when the output gate closes and all the electric charge transferred flows into the floating diffusion 9, and the signal at this time becomes the true signal. This signal IV is transformed into the output signal consisting of the true signal only by using the sample and hold circuit (not illustrated), and is outputted to the outside. This external output is inputted to the monitor 27 (see FIG. 6) and visualized.

Referring now to FIGS. 15A–15E and FIGS. 16A–16E, the manufacturing process of the two-dimensional pH distribution measuring equipment is described. This process is only one example, and the device fabricated by this process uses an electric charge transferring system of the surface channel.

Figure 15A:
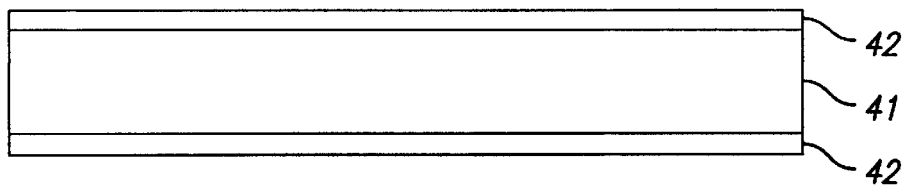
FIGS. 15A–15E are schematic views showing one example of the manufacturing process of the equipment according to the first embodiment together with FIG. 16.

(1) First of all, a p-type Si wafer 41 of about 10 Ω-cm resistivity is wet-oxidized at 1100° C. for about 90 minutes using a thermal oxidization furnace, and oxide film (field oxide film) 42 of about 6000 Å is formed on both top and bottom surfaces (see FIG. 15A).

Figure 15B:
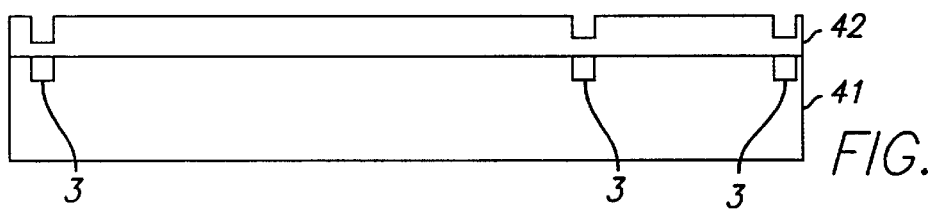
Figure 15C:
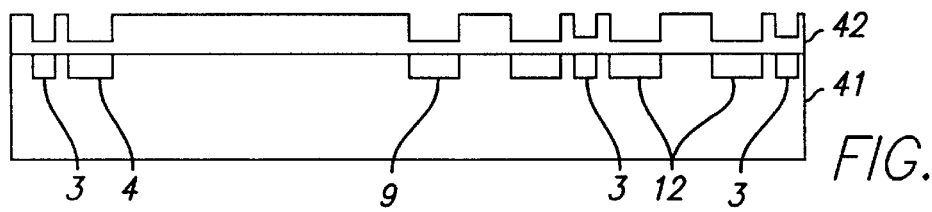
Figure 15D:
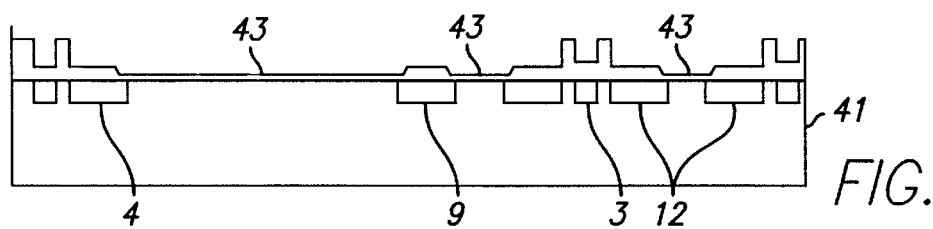
Figure 15E:
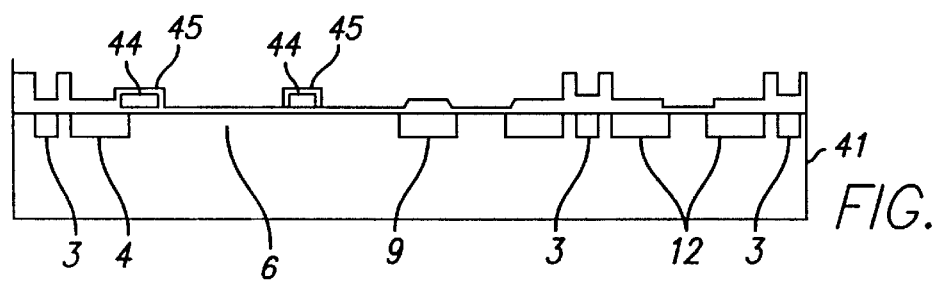

(2) Then, channel stoppers 3 are formed (see FIG. 15B). The method for forming the channel stopper 3 is to etch the field oxide film 42 at the stopper forming places using hydrofluoric acid (HF), and to diffuse boron (B) at the places. The method for diffusing boron is, for example, to predeposition the solid diffusion source at 1100° C. for 15 minutes together with the wafer 41, then after removing the borosilicate glass, to drive-in oxidize at 1140° C. for about 1 hour, and then to anneal in the nitrogen gas atmosphere for about 10 minutes.

(3) The electric charge feeder section 4, the floating diffusion 9, and the source and the drain of the output transistor 12 are n-type diffusion regions (see FIG. 15C), and these are formed in the same manner as in the case of channel stoppers 3 with the exception that the liquid phosphorous diffusion source is used for a diffusion source, and are formed in order of predeposition, drive-in oxidation, and annealing.

(4) The electric charge injection controller section 5, the sensing section 6, barrier section 7, and the electric charge transferring section 8 must have the oxide film made thinner in order to allow the potential of the electrodes to exert great influences on the oxide film and the semiconductor interface. Consequently, as shown in FIG. 15 (D), the field oxide 42 corresponding to these sections are etched with hydrofluoric acid, and then it is oxidized at 1050° C. for about 2.5 hours, and annealed for about 20 minutes in the nitrogen gas atmosphere to form the gate oxide film 43 in thickness of about 1000 Å.

(5) For the electrode, as already described, the P-doped low-resistance poly-silicon is used. First of all, using chemical vapor deposition (CVD), P-doped low-resistance poly-silicon is deposited to about 3000 Å. Using a photo-lithography, poly-silicon other than the electrode forming portions is etched with the reactive ion etching machine. Thereafter, poly-silicon is oxidized at 1140° C. for about 45 minutes to cover the poly-silicon electrodes 44 at the electrode forming portions with the oxide film 45 at about 1000 Å (see FIG. 15E). The oxide film 45 is provided for insulating from the other poly-silicon electrode 46 formed by depositing an additional poly-silicon film in the next process (see FIG. 16A).

Figure 16A:
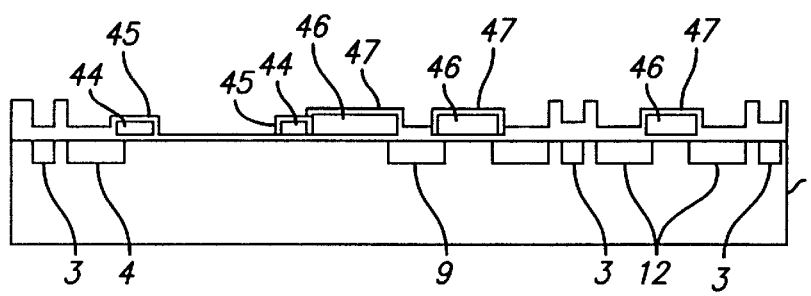
FIGS. 16A–16E are schematic views showing one example of the manufacturing process of the equipment according to the first embodiment together with FIG. 15.
Figure 16B:
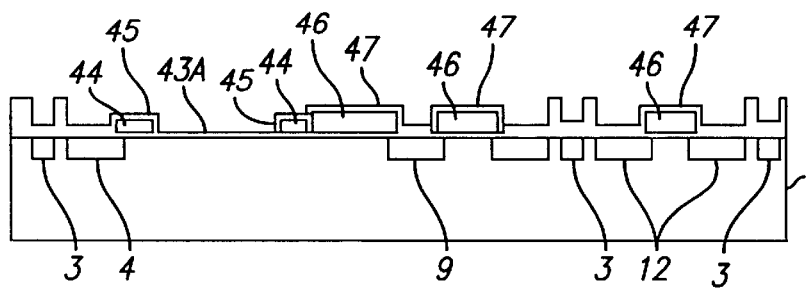
Figure 16C:
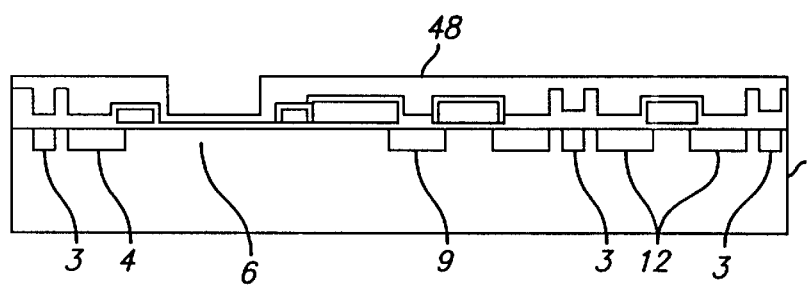

(6) Then poly-silicon is deposited in the similar process to the above, and the electrodes 46 are formed by carrying out patterning, and the poly-silicon electrodes 46 are further covered with the oxide film 47 (see FIG. 16A). This oxide film 47 is to successfully affix the nitride film ($Si_3N_4$) 48 in the subsequent process (see FIG. 16C).

(7) Now the oxide film 43 at the portion where the sensing section 6 is formed is degraded after passing various processes after gate oxidation. Therefore, this oxide film 43 is removed by the use of hydrofluoric acid and the gate oxide 43A of about 1000 Å is newly formed (see FIG. 16B).

(8) In order to provide pH sensitivity and water resisting property, the nitride film 48 is deposited to about 800 Å using CVD (see FIG. 16 (C)).

Figure 16D:
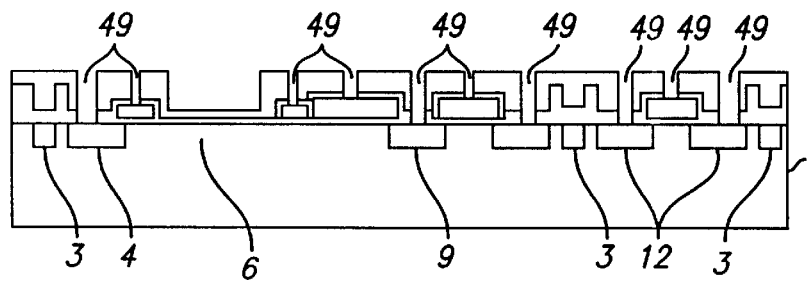

(9) Contact holes 49 are opened so that voltage can be applied from the outside to each of the electrodes and n-diffused layers, respectively (see FIG. 16D).

Figure 16E:
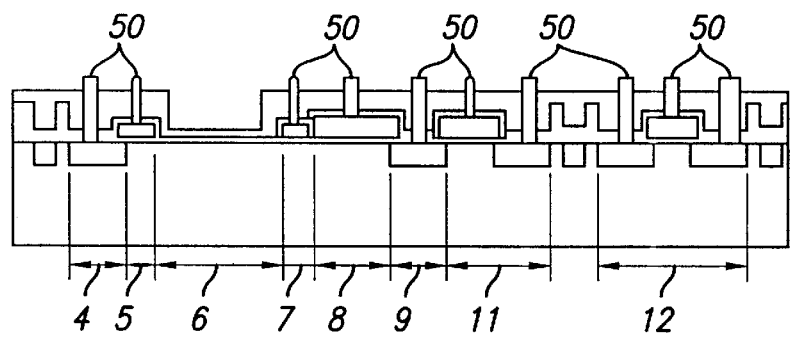

(10) In order to deposit aluminum to about 1 μm to form electrodes 50 at the portions where contact holes 49 are formed, electrode patterns are formed by photo-lithography, and portions other than these portions are etched (see FIG. 16E).

In the above fabrication method, since the surface channel is employed in which the electric charge transfer takes place at the semiconductor 41 surface, the transfer efficiency was about 98%, but as the number of pixels increases, the transfer loss becomes a problem. Therefore, when the number of pixels increases, it is preferable to use the bulk channel system in which electric charge transfer takes place inside the semiconductor 41.

According to the pH two-dimensional distribution measuring equipment of the above-configuration, the pH at a plurality of positions of different solutions can be simultaneously measured. Since the pH simultaneously measured is converted to electric charges, the two-dimensional distribution of pH can be easily visualized by transferring the electric charges using the techniques such as CCD.

In the above-mentioned embodiment, two-dimensional distribution of pH was intended to be measured, but by chemically modifying the surface of the sensing section 6 with suitable sensitive material, the ion concentration other than pH can be measured. That is, this invention can be suitably and extensively used for two-dimensional distribution measurement of ion concentration of samples, such as solutions, as well as applied to the following fields:

(1) Applicable fields as a chemical microscope:
   (a) Chemical; ion concentration measurement;
   (b) Electro-chemical field, gas distribution measurement field; and
   (c) Two-dimensional observation and analysis of titration;
(2) Environment measurement:
   (a) Environment: application to bioremediation;
(3) Food inspection
   (a) Foods, microorganisms;
(4) ME field:
   (a) Medical and ecological tissues: surface ion concentration; and
   (b) measurement, cell surface potential measurement;
(5) Animal and plant field:
   (a) Plants: surface potential distribution measurement of callus; and
   (b) Living being/front view animals;
(6) Corrosion measuring field:
   (a) Metal: painting and coating of metal corrosion; and
(7) Surface analysis such as zeta potential, etc.:
   (a) Zeta potential of powders and ceramics.

The measurement subjects (samples) may be gas, liquid, solid, or powders. The embodiment can be applied to chemical sensing which selectively reacts by the specific sensitive layer of the sensor section as well as to any phenomena in which electric particles fluctuate at the interface by physical contact. For example, the distribution of liquid flow or the distribution of transient phenomena of instantaneous chemical reactions can be obtained in the form of high-sensitivity, high-quality chemical images. In addition, the embodiment is useful from real-time visualization of titration phenomena to other kinds of analysis and display by image software.

For a second embodiment, a two-dimensional distribution measurement of pressure using a pressure sensor is described. FIG. 17 schematically shows one example of two-dimensional distribution measuring equipment of pressure. In FIG. 17, numeral 60 designates a p-type Si substrate, and numeral 61 is an n-well region of 1 µm or less formed at the surface of the substrate 60. Numeral 62 is a p+ diffusion layer formed in the n-well region 61, and is an emitter doped at the concentration higher than that in the substrate 60. On this p+ diffusion layer 62, a thick oxide film about 1 µm thick is provided, and stress is focused on the emitter of this pnp transistor.

On the p+ diffusion layer 62, a contact hole is formed to install a metal electrode 63 to sweep up to the gate of the sensing section 64, and the potential of the p+ diffusion layer 62 is applied to the sensing section 64. The oxide film only of this sensing section 64 is made to be 1000 Å thick, and the oxide film around it is made to be 5000 Å thick. This is to greatly vary the potential in the vicinity of the interface between the semiconductor and the oxide film for the sensing section 64 only by the potential of the metal electrode 63. Numeral 65 designates channel stoppers formed surrounding the circumference of the sensing section 64, and potentially separate the sensing section 64 from the circumference. Numeral 66 is an insulator, and numeral 67 is a power supply that biases in the reverse direction across the substrate 60, the collector, and the n-well region 61, the base. Though not illustrated, an electric charge feeder section, a barrier section, etc. are provided perpendicular to the paper surface.

In the two-dimensional distribution measuring equipment of pressure, when mechanical stress 68 is exerted to the pnp transistor in the direction perpendicular to the pnp junction surface, voltage across the emitter and the base varies and the potential of the emitter section 62 varies. This potential change is swept to the sensing section 64 using the metal electrode. By this change of the swept potential, the potential at the interface between the oxide film and the semiconductor of the sensing section 64 varies, and by injecting electric charges to it, the change in the potential is converted to the electric charges amount.

For a third embodiment, a magnetic field two-dimensional distribution measuring equipment is explained. For this magnetic field measurement, the Hall effect is utilized. First of all, FIG. 18 is an illustration schematically describing the measuring principle of the two-dimensional magnetic field distribution. Insulating material 71 is accumulated on the top surface of a semiconductor substrate 70, and a semiconductor 72 is further accumulated on the top surface, with current being allowed to flow in this semiconductor 72 in the direction of arrow 73. When the substrate 70 is set in such a manner that the magnetic field direction 100 crosses at right angles to the direction of the current 73 and is parallel to the substrate 70, voltage is generated in the direction perpendicular to the surface of the substrate 70. And the two-dimensional distribution of the magnetic field can be measured by converting the magnitude of this voltage to electric charges by the above-mentioned electric charge conversion mechanism.

Figure 19A:
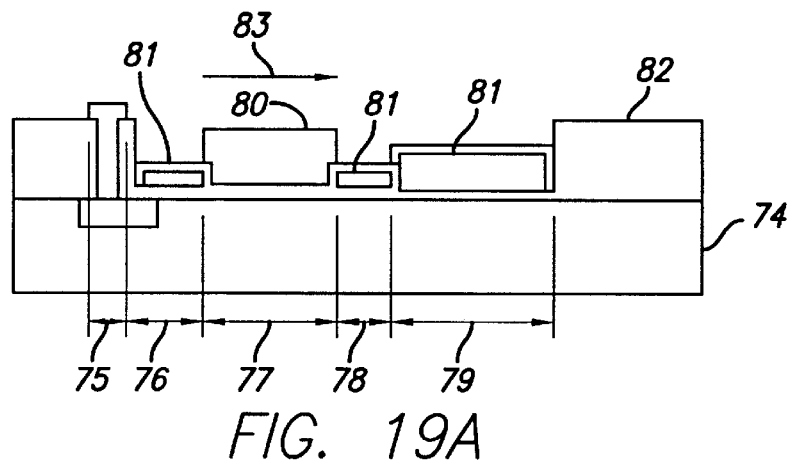
FIG. 19A is a longitudinal cross-sectional schematic view showing the equipment according to a third embodiment.
Figure 19B:
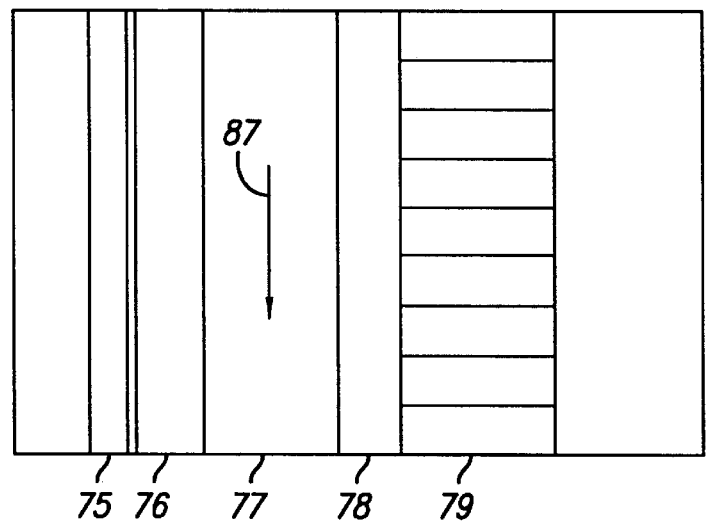
FIG. 19B is a plan view of the equipment shown in FIG. 19B.

FIGS. 19A and 19B schematically show the construction of the sensor section of the magnetic field two-dimensional distribution measuring equipment configured on the basis of the measuring principle mentioned above, with FIG. 19A showing a cross-sectional structure and FIG. 19B showing a plane structure. In FIGS. 19A and 19B, numeral 74 designates a semiconductor substrate; 75, an electric charge feeder section; 76, an electric charge injection controller section; 77, a sensing section; 78, a barrier section; and 79, an electric charge transfer section.

Numeral 80 is an epitaxial grown Si layer deposited only on the top surface of the sensing section 77; numeral 81 is electrodes comprising poly-silicon; and numeral 82 is an insulation layer comprising an epitaxial grown $Al_2O_3$ insulation layer. The thickness of the $Al_2O_3$ layer is set to about 1000 Å at the bottom of the Si layer 80 and the poly-silicon electrodes 81, respectively, and is configured in such a manner that fluctuation of potential is positively generated.

Now, if the magnetic field is in the direction shown with arrow 83, when the current is allowed to flow in the Si layer 80 as shown with arrow 84, voltage by the magnetic field 83 is generated in the direction perpendicular to the semiconductor substrate 74, and the potential in the vicinity of the interface between the semiconductor 70 and the insulation layer 82 comprising $Al_2O_3$ fluctuates. The magnetic field two-dimensional distribution can be measured by converting this potential fluctuation into electric charges using the electric-charge conversion mechanism.

Figure 20:
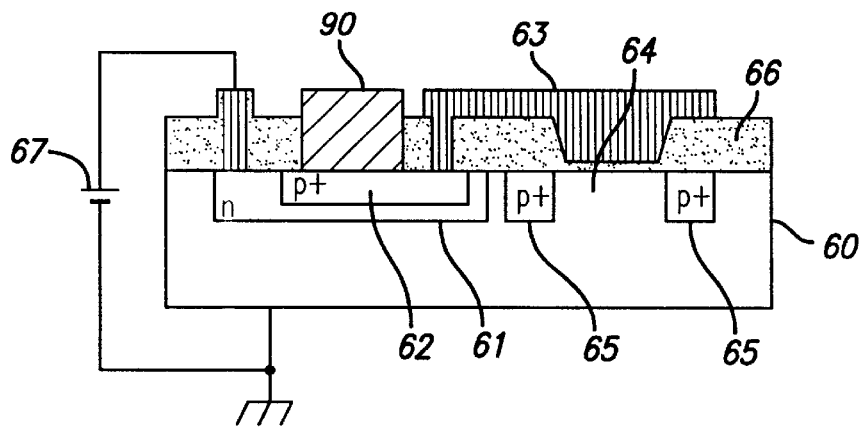
FIG. 20 is a longitudinal cross-sectional view schematically showing the equipment according to a fourth embodiment.

For a fourth embodiment, a two-dimensional temperature distribution measuring equipment will be described. In this measuring equipment, the phenomenon in that the voltage across the emitter and the base of the pnp transistor varies by the change of temperature is utilized. This is nearly similar to the pressure two-dimensional distribution measuring equipment of the second embodiment (see FIG. 17) in this point. Consequently, in FIG. 20, which schematically shows the two-dimensional temperature distribution measuring equipment, like reference characters designate like or corresponding parts in FIG. 17. However, what is different is that temperature at a small area is given to the emitter 62 by bringing a metal 90 with good thermal conductivity in contact with the emitter 62. Therefore, by supplying the generated voltage to the sensing section 64 and converting it to electrical charges using the electric charge conversion mechanism, the two-dimensional temperature distribution can be measured.

Other physical phenomena or chemical phenomena, in almost all cases, can be converted to electrical signals such as voltage, current, etc., and converting these electrical signals to electric charges using the electric charge conversion mechanism, special handling of the electric charges can be achieved.

Each of the above-mentioned embodiments is intended to measure the two-dimensional distribution with respect to some specific physical phenomena or chemical phenomena by arraying the same sensor, but this invention shall not be limited to these. By arraying a plurality of sensors of different kinds, a plurality of physical phenomena or chemical phenomena can be simultaneously measured.

Figure 21:
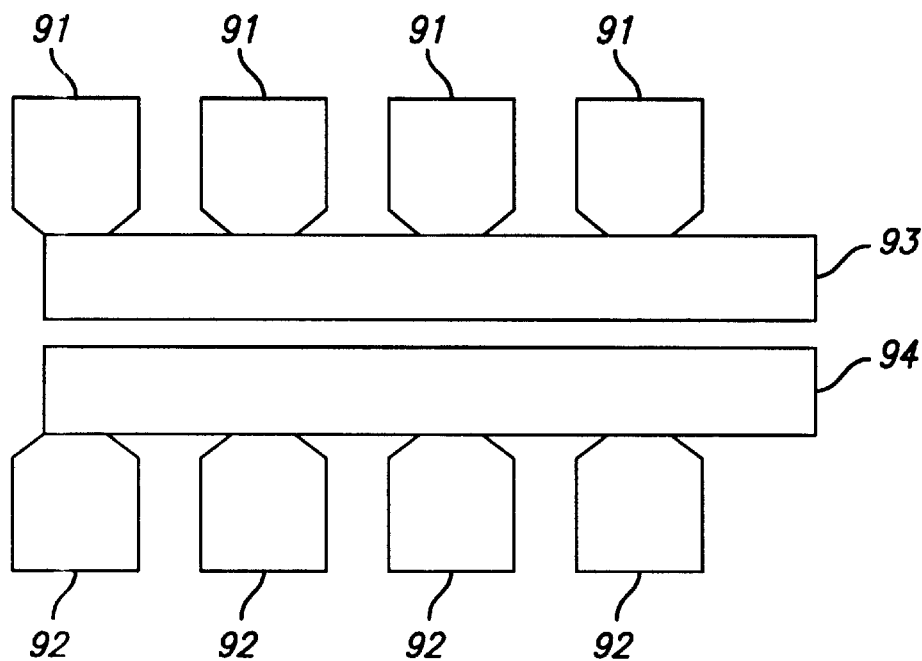
FIG. 21 is a schematic view showing another embodiment.

For example, as shown in FIG. 21, by bringing and arranging a plurality of the sensor sections 91 for measuring the pH and the sensor sections 92 for measuring temperature closer to one another and transferring electric charges obtained by relevant sensor sections 91, 92 using independent electric charge transfer sections 93, 94, respectively, the two-dimensional distributions of pH and temperature can be obtained simultaneously.

Figure 22:
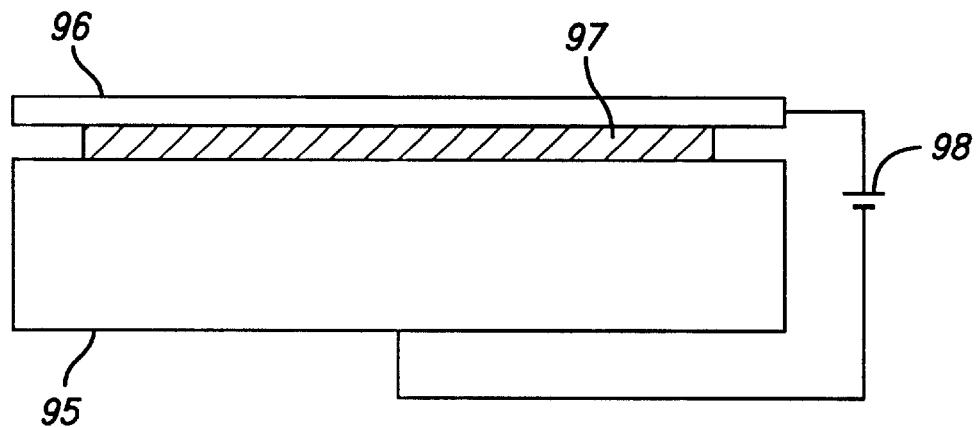
FIG. 22 is a schematic view showing still another embodiment.

As shown in FIG. 22, an electrode 96 is installed throughout the full surface of the top surface of a device 95, and a sample 97 (any of solid, liquid, or gas) is located in the form of sandwich between this electrode 96 and the device 95, and voltage is applied across the device 95 and the electrode 96 under this condition. By this contrivance, the sample with different resistivity 97 gives potentials varying at relevant positions to the device 95. By converting this voltage to electric charges, it is possible to detect the two-dimensional distribution of the sample 97. Numeral 98 designates the bias power supply in this figure.

According to the measuring method of the physical phenomena or chemical phenomena of this invention, phenomena in multiple different positions can be simultaneously detected. And since the physical or chemical quantity is converted to the electric charges, the two-dimensional distribution of the physical or the chemical phenomena can be easily visualized by the use of a CCD. Depending on the data processing method, it is also possible to obtain the three-dimensional distribution.

Because amplification of weak signals is possible by accumulating electric charges representing information of a plurality of points, it is possible to positively grasp microscopic changes of the phenomena.

What is claimed is:

1. Apparatus for measuring physical or chemical phenomena, said apparatus comprising:

a plurality of potential wells constructed to be variable in depth in accordance with a magnitude of a physical or a chemical quantity;

wherein when electrical charge is injected in said potential wells, a physical or a chemical quantity is converted into electrical charge in accordance with a depth of said potential wells.

2. The apparatus of claim 1, further comprising a substrate, said plurality of potential wells disposed within said substrate.

3. The apparatus of claim 2, wherein said substrate is a semiconductor substrate.

4. The apparatus of claim 3, wherein said semiconductor substrate is a MOS device.

5. The apparatus of claim 1, further comprising:

a plurality of sensor sections;

each of said plurality of sensor sections including said plurality of potential wells;

wherein said plurality of sensor sections are configured in a two-dimensional array.

6. The apparatus of claim 5, further comprising an imaging system coupled to an output of said plurality of sensor sections to generate a two-dimensional image.

7. The apparatus of claim 6, further comprising a charge coupled device coupled to said output of said plurality of sensor sections.

8. The apparatus of claim 1, further comprising:

a plurality of sensor sections;

each of said plurality of sensor sections including said plurality of potential wells;

wherein said plurality of sensor sections are configured in a one-dimensional array.

9. The apparatus of claim 5, further comprising an imaging system coupled to an output of said plurality of sensor sections to generate a one-dimensional image.

10. The apparatus of claim 9, further comprising a charge coupled device coupled to said output of said plurality of sensor sections.

11. The apparatus of claim 1, further comprising:

a substrate having a sensor section and an output section;

said plurality of potential wells disposed within said sensor section; and said output section coupled to said sensor section.

12. The apparatus of claim 11, wherein said sensor section includes an electric charge feeder section, an electric charge injection controller section, a sensing section, and a barrier section, wherein said plurality of potential wells are disposed within said sensing section.

13. The apparatus of claim 11, wherein said output section includes a floating diffusion, a reset gate, a reset drain, and an output transistor.

14. The apparatus of claim 1, further comprising:

a source follower circuit coupled to said plurality of potential wells; and an image output unit to image an output of said source follower circuit.

15. The apparatus of claim 1, wherein said chemical quantity is pH.

16. The apparatus of claim 1, wherein said physical quantity is temperature.

17. The apparatus of claim 1, wherein said physical quantity is a magnetic field.

18. The apparatus of claim 1, further comprising:

a plurality of sensor sections;

each of said plurality of sensor sections including said plurality of potential wells;

wherein a first portion of said plurality of sensor sections are adapted to measure physical phenomena and a second portion of said plurality of sensor sections are adapted to measure chemical phenomena.

19. The apparatus of claim 18, wherein said chemical phenomena includes pH, and said physical phenomena include temperature, magnetic field, and pressure.

20. The apparatus of claim 1, further comprising:
   a substrate, said plurality of potential wells disposed within said substrate;
   a cell containing a sample fluid, wherein said substrate forms a bottom portion of said cell such that said substrate is in direct contact with said sample fluid;
   a reference electrode disposed in said cell and directly contacting said sample fluid; and
   a power supply coupled to said substrate and said reference electrode.

21. Apparatus for measuring physical or chemical phenomena, said apparatus comprising:
   a plurality of potential wells constructed to be variable in depth in accordance with a magnitude of a physical or a chemical quantity, said potential wells disposed one-dimensionally;
   wherein when electrical charge is injected in said potential wells, a physical or a chemical quantity is converted into electrical charge in accordance with a depth of said potential wells.

22. The apparatus of claim 21, wherein said physical phenomena is a magnetic field, and wherein a magnitude b of said magnetic field B is determined in accordance with a variation in depth of said potential wells.

23. Apparatus for measuring physical or chemical phenomena, said apparatus comprising:
   a plurality of potential wells constructed to be variable in depth in accordance with a magnitude of a physical or a chemical quantity, said potential wells disposed two-dimensionally;
   wherein when electrical charge is injected in said potential wells, a physical or a chemical quantity is converted into electrical charge in accordance with a depth of said potential wells.

24. The apparatus of claim 23, wherein said physical phenomena is a magnetic field, and wherein a magnitude b of said magnetic field B is determined in accordance with a variation in depth of said potential wells.

* * * * *